US009625423B2

(12) United States Patent
Bossi et al.

(10) Patent No.: US 9,625,423 B2
(45) Date of Patent: Apr. 18, 2017

(54) SYSTEM AND METHOD FOR TESTING A COMPOSITE STRUCTURE USING A LASER ULTRASOUND TESTING SYSTEM

(71) Applicant: The Boeing Company, Chicago, IL (US)

(72) Inventors: Richard H. Bossi, Renton, WA (US); Gary Ernest Georgeson, Tacoma, WA (US); Jeffrey Reyner Kollgaard, Seattle, WA (US); Alan Frank Stewart, Renton, WA (US); William P. Motzer, Seattle, WA (US); Clarence Lavere Gordon, III, Renton, WA (US); Matthew O'Donnell, Seattle, WA (US); Jinjun Xia, Seattle, WA (US); Ivan Pelivanov, Seattle, WA (US); Chen-wei Wei, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 1048 days.

(21) Appl. No.: 13/663,855

(22) Filed: Oct. 30, 2012

(65) Prior Publication Data

US 2014/0116146 A1 May 1, 2014

(51) Int. Cl.
*G01N 29/24* (2006.01)
*G01N 29/22* (2006.01)
*G01N 29/34* (2006.01)

(52) U.S. Cl.
CPC ....... *G01N 29/225* (2013.01); *G01N 29/2418* (2013.01); *G01N 29/343* (2013.01); *G01N 2291/0231* (2013.01)

(58) Field of Classification Search
CPC ....... G01N 29/2418; G01N 2291/0231; G01N 21/1702; G01N 21/1706; G01N 2021/0156; G10K 15/046
USPC .......................................... 73/643, 655, 657
See application file for complete search history.

(56) References Cited

U.S. PATENT DOCUMENTS

| 4,379,409 | A | * | 4/1983 | Primbsch et al. ............. 73/643 |
| 5,099,693 | A | * | 3/1992 | Payne ................ G01N 29/2418 73/632 |
| 2005/0120803 | A1 | * | 6/2005 | Sokol et al. ..................... 73/801 |
| 2009/0010285 | A1 | * | 1/2009 | Dubois et al. ..................... 372/3 |
| 2009/0156932 | A1 | * | 6/2009 | Zharov ................ A61B 5/0059 600/437 |

OTHER PUBLICATIONS

Anastasi et al., "Pulse Compression Techniques for Laser Generated Ultrasound," Proceedings of the 1999 IEEE Ultrasonics Symposium, vol. 1, Oct. 1999, 5 pages.
(Continued)

*Primary Examiner* — Laura Martin
*Assistant Examiner* — Rose M Miller
(74) *Attorney, Agent, or Firm* — Yee & Associates, P.C.

(57) ABSTRACT

A method and apparatus for testing a composite structure. A pulsed laser beam having a number of properties is generated. Each of the number of properties is within a selected range. The pulsed laser beam generated by the generation laser system is directed towards a composite structure comprised of a number of composite materials. A number of ultrasonic waves are formed in the composite structure when the pulsed laser beam contacts the composite structure without causing any undesired inconsistencies in the composite structure outside of selected tolerances.

15 Claims, 3 Drawing Sheets

(56) References Cited

OTHER PUBLICATIONS

Dubois et al., "Progress on the Development of an Advanced Laser Ultrasound Generation Source for Inspecting Polymer-Matrix Composites," AIP Conference Proceedings, vol. 615, May 2002, pp. 300-307.

Georgeson et al., "Ultrasound Inspection System of Limited Access Composite Structures," U.S. Appl. No. 13/526,698, filed Jun. 19, 2012, 74 pages.

Bossi et al., "Ultrasound Inspection System for Inspecting a Test Object with Non-Planar Features," U.S. Appl. No. 13/526,853, filed Jun. 19, 2012, 62 pages.

Bossi et al., "Laser Ultrasound Array System," U.S. Appl. No. 13/527,021, filed Jun. 19, 2012, 62 pages.

Yawn et al., "Large-Scale Laser Ultrasonic Facility for Aerospace Applications," Review of Progress in Quantitavive Nondestructive Evaluation, vol. 18, edited by Thompson and Chimenti, Kluwer Academic/Plenum Publishers, May 1999, pp. 387-393.

\* cited by examiner

SYSTEM AND METHOD FOR TESTING A COMPOSITE STRUCTURE USING A LASER ULTRASOUND TESTING SYSTEM

BACKGROUND INFORMATION

1. Field

The present disclosure relates generally to ultrasound testing and, in particular, to ultrasound testing of composite structures. Still more particularly, the present disclosure relates to a system and method for testing a composite structure using a laser ultrasound testing system.

2. Background

A composite structure, as used herein, may be any structure comprised of at least one composite material. The composite material may include a matrix material and a reinforcement material. Composite structures may be inspected using different types of testing systems. A laser ultrasound testing (UT) system is an example of one type of testing system that may be used to test a composite structure for undesired inconsistencies. Laser ultrasound testing allows a composite structure to be tested without the testing system physically contacting the composite structure.

Typically, a laser ultrasound testing system uses a pulsed laser beam to generate ultrasonic waves in a composite structure. A pulsed laser beam is a beam formed by pulses of laser energy that are emitted at some selected pulse repetition rate. The laser ultrasound testing system is capable of detecting these ultrasonic waves and using the detected ultrasonic waves to generate data about the composite structure. This data may be used to identify information about the composite structure such as, for example, without limitation, a thickness of the composite structure, a material composition of the composite structure, an indication of whether any undesired inconsistencies are present on and/or in the composite structure, and/or other types of information.

With some currently available laser ultrasound testing systems, a gas laser source is used to generate a pulsed laser beam that has a spot size of about five millimeters (mm). The spot size is the size of the area on the surface of a composite structure that is illuminated by the laser beam. In some situations, a spot size of about five millimeters may not be small enough to allow a finer level of detail to be characterized with respect to the composite structure.

Further, with some currently available laser ultrasound testing systems, the scanning rate, or rate at which the pulsed laser beam may be moved along the surface of the composite structure, is determined by the pulse repetition rate of the laser ultrasound testing system. Some currently available laser ultrasound testing systems may be unable to generate a pulsed laser beam with a pulse repetition rate high enough to provide a scanning rate within selected tolerances. Additionally, the size, weight, and/or cost of some currently available laser ultrasound testing systems that use gas laser sources may be greater than desired. Further, the size and/or weight of these types of laser ultrasound testing systems may require that testing be performed in an area or room that has shielding or some other type of protection. Therefore, it would be desirable to have a method and apparatus that takes into account at least some of the issues discussed above, as well as other possible issues.

SUMMARY

In one illustrative embodiment, a laser ultrasound testing system comprises a generation laser system and a transmission system. The generation laser system is configured to generate a pulsed laser beam having a number of properties in which each of the number of properties is within a selected range. The transmission system is configured to direct the pulsed laser beam generated by the generation laser system towards a composite structure comprised of a number of composite materials. A number of ultrasonic waves are formed in the composite structure when the pulsed laser beam contacts the composite structure without causing any undesired inconsistencies in the composite structure outside of selected tolerances.

In another illustrative embodiment, a method for testing a composite structure is provided. A pulsed laser beam having a number of properties is generated. Each of the number of properties is within a selected range. The pulsed laser beam generated by a generation laser system is directed towards the composite structure comprised of a number of composite materials. A number of ultrasonic waves are formed in the composite structure when the pulsed laser beam contacts the composite structure without causing any undesired inconsistencies in the composite structure outside of selected tolerances.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account different considerations. For example, the illustrative embodiments recognize and take into account that it may be desirable to have a laser ultrasound testing system capable of testing a composite structure without causing undesired inconsistencies in and/or on the composite structure outside of selected tolerances.

Further, the illustrative embodiments recognize and take into account that generating a pulsed laser beam with a pulse repetition rate above about 10,000 hertz (Hz) and a spot size less than about 1 millimeter (mm) may allow an increased scanning rate when testing a composite structure. Additionally, the illustrative embodiments recognize and take into account that absorption of laser energy into a reinforcement material in a composite material may cause ultrasonic waves to be generated more efficiently than absorption into a matrix material in the composite material.

Thus, the illustrative embodiments provide a system and method for testing a composite structure using a pulsed laser beam. In one illustrative embodiment, a laser ultrasound testing system comprises a generation laser system and a transmission system. The generation laser system is configured to generate a pulsed laser beam having a number of properties in which each of the number of properties is within a selected range. The transmission system is configured to direct the pulsed laser beam generated by the generation laser system towards a composite structure comprised of a number of composite materials. A number of ultrasonic waves are formed in the composite structure when the pulsed laser beam contacts the composite structure without causing any undesired inconsistencies in the composite structure outside of selected tolerances.

Figure 1:
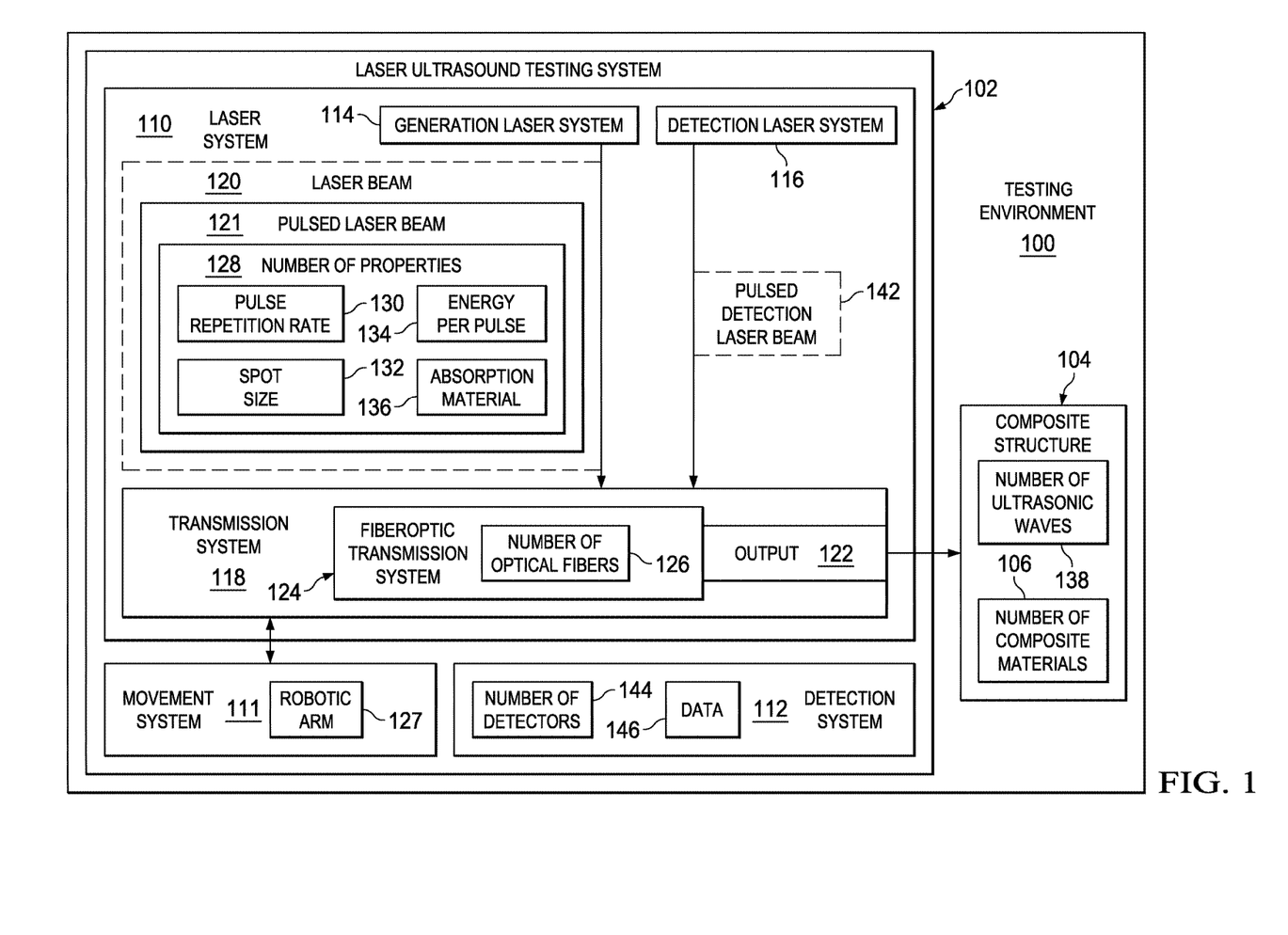
FIG. 1 is an illustration of a testing environment in the form of a block diagram in accordance with an illustrative embodiment.

With reference now to FIG. 1, an illustration of a testing environment in the form of a block diagram is depicted in accordance with an illustrative embodiment. In FIG. 1, testing environment 100 is an example of an environment in which laser ultrasound testing system 102 may be used to test composite structure 104.

Composite structure 104 may be comprised of number of composite materials 106. As used herein, a "number of" items means one or more materials. In this manner, number of composite materials 106 may include one or more composite materials. Each of these composite materials may be comprised of a matrix material and a reinforcement material.

As one illustrative example, the matrix material takes the form of a resin and the reinforcement material takes the form of fibers. Of course, in other illustrative examples, other types of matrix materials and/or reinforcement materials may make up a composite material in number of composite materials 106. Further, in some illustrative examples, composite structure 104 may include one or more materials in addition to number of composite materials 106.

In these illustrative examples, laser ultrasound testing system 102 is considered a nondestructive testing (NDT) system. As depicted, laser ultrasound testing system 102 includes laser system 110, movement system 111, and detection system 112. Laser system 110 includes generation laser system 114, detection laser system 116, and transmission system 118.

Generation laser system 114 is configured to generate laser beam 120. In one illustrative example, laser beam 120 takes the form of pulsed laser beam 121. Pulsed laser beam 121 is formed by pulses of laser energy. In other words, pulsed laser beam 121 is formed by pulses of light that are emitted in the form of a beam.

Pulsed laser beam 121 emitted by generation laser system 114 may be sent into transmission system 118. Transmission system 118 is configured to transmit pulsed laser beam 121 through output 122 of transmission system 118.

In these illustrative examples, transmission system 118 takes the form of a fiberoptic transmission system 124. Fiberoptic transmission system 124 may include number of optical fibers 126. Pulsed laser beam 121 may be carried from generation laser system 114 to output 122 of transmission system 118 through at least a portion of number of optical fibers 126.

As depicted, movement system 111 may be associated with transmission system 118. When one component is "associated" with another component, the association is a physical association in the depicted examples.

For example, a first component, such as movement system 111, may be considered to be associated with a second component, such as transmission system 118, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Movement system 111 is configured to manipulate transmission system 118 such that pulsed laser beam 121 emitted from output 122 of transmission system 118 is directed along a desired path along composite structure 104. In some cases, output 122 of transmission system 118 may also be an output of movement system 111.

In one illustrative example, movement system 111 takes the form of robotic arm 127. Number of optical fibers 126 may run through robotic arm 127. Robotic arm 127 may move in a manner that allows pulsed laser beam 121 to be moved along composite structure 104. In other words, robotic arm 127 may allow pulsed laser beam 121 to scan composite structure 104 along a desired path.

Generation laser system 114 is configured to generate pulsed laser beam 121 having number of properties 128 in which each property in number of properties 128 is within a selected range. The selected range for each property in number of properties 128 may be selected such that pulsed laser beam 121 is generated in a manner that causes number of ultrasonic waves 138 to be formed in composite structure 104 when pulsed laser beam 121 encounters composite structure 104 without causing any undesired inconsistencies in composite structure 104 outside of selected tolerances.

Number of properties 128 may include for example, without limitation, pulse repetition rate 130, spot size 132, energy per pulse 134, absorption material 136, and/or other properties. Each of these properties may have values within selected ranges.

Pulse repetition rate 130 is the rate at which the pulses of laser energy are emitted to form pulsed laser beam 121. Pulse repetition rate 130 may be described in terms of, for example, without limitation, frequency. In these illustrative examples, generation laser system 114 is configured to generate pulsed laser beam 121 such that pulsed laser beam 121 has pulse repetition rate 130 between about 10,000 hertz (Hz) and about 500,000 hertz (Hz). A pulse repetition rate within this range may be considered a high pulse repetition rate.

Further, the selected range for pulse repetition rate 130 is selected such that pulse repetition rate 130 is sufficiently high to allow the rate at which pulsed laser beam 121 is moved along composite structure 104 to be within selected tolerances. In particular, a high value for pulse repetition rate 130 allows the rate at which pulse repetition rate 130 scans composite structure 104 to be high as well. In other words, as pulse repetition rate 130 increases, the scanning rate may also increase.

Spot size 132 is the size of the area on the surface of composite structure 104 illuminated by pulsed laser beam 121. In these illustrative examples, generation laser system 114 is configured to generate pulsed laser beam 121 such that spot size 132 is less than about 1 millimeter (mm). A spot size less than about 1 millimeter (mm) may be considered a small spot size in these examples.

The selected range for spot size 132 of pulsed laser beam 121 is selected such that the path formed by pulsed laser beam 121 as pulsed laser beam 121 scans composite structure 104 has a width that is sufficiently narrow to allow smaller features of composite structure 104 to be characterized.

Further, energy per pulse 134 may be the amount of energy contained within each pulse of laser energy that forms pulsed laser beam 121. Pulsed laser beam 121 is generated such that energy per pulse 134 is within a range that is selected to allow number of ultrasonic waves 138 to be formed in composite structure 104 without causing a number of inconsistencies in composite structure 104 outside of selected tolerances. In these illustrative examples, generation laser system 114 is configured to generate pulsed laser beam 121 such that energy per pulse 134 is within the range of about 1 microjoule (µJ) to about 10,000 microjoules (µJ).

In these illustrative examples, the combination of spot size 132 and energy per pulse 134 may be used to produce an optical fluence within a desired range. As used herein, "fluence" may be the energy transferred through a unit area. Pulsed laser beam 121 may be generated such that the optical fluence per pulse ranges between about 0.1 millijoules per centimeters squared (mJ/(cm$^2$)) to about 1000 millijoules per centimeters squared (mJ/(cm$^2$)). The value within this range selected for the optical fluence per pulse may be selected such that pulsed laser beam 121 does not cause any inconsistencies on and/or in composite structure 104 outside of selected tolerances.

Absorption material 136 may be the constituent material in number of composite materials 106 into which at least a portion of the energy in pulsed laser beam 121 is absorbed. Absorption material 136 may also be referred to as a principal absorption material. In these illustrative examples, pulsed laser beam 121 is generated such that at least a portion of the energy in pulsed laser beam 121 is absorbed into a reinforcement material in number of composite materials 106 instead of a matrix material in number of composite materials 106.

A reinforcement material in number of composite materials 106 may have a higher modulus than a matrix material in number of composite materials 106. Further, the reinforcement material may be surrounded by the matrix material and thus, constrained by the matrix material. Consequently, absorbing the energy in pulsed laser beam 121 into the reinforcement material allows increased spatial localization and conversion of energy into number of ultrasonic waves 138. Further, this type of conversion may lead to a higher frequency content in number of ultrasonic waves 138. The higher frequency content may, in turn, allow information of a finer level of detail about composite structure 104 to be characterized using number of ultrasonic waves 138 as compared to using ultrasonic waves having lower frequency content.

As depicted, detection laser system 116 is configured to generate pulsed detection laser beam 142. Pulsed detection laser beam 142 may be transmitted through transmission system 118 and emitted from output 122 of transmission system 118. Pulsed detection laser beam 142 may be directed towards composite structure 104 at a location selected such that number of ultrasonic waves 138 generated in composite structure 104 may be detected.

For example, when pulsed detection laser beam 142 encounters at least one ultrasonic wave in number of ultrasonic waves 138, the path of pulsed detection laser beam 142 may be altered. This alteration may be detected by detection system 112. Detection system 112 may include, for example, without limitation, number of detectors 144. In one illustrative example, number of detectors 144 may be a number of photodetectors.

Number of detectors 144 is configured to detect laser energy. Detection system 112 generates data 146 in response to the detection of this laser energy. Data 146 may be used to identify information about composite structure 104. This information may include, for example, without limitation, a thickness of composite structure 104, a material composition of composite structure 104, an indication of whether any undesired inconsistencies are present on and/or in composite structure 104, and/or other types of information.

In these illustrative examples, data 146 generated by detection system 112 may be comprised of a plurality of data points. Increasing the number of data points included in data 146 may allow a higher signal-to-noise ratio to be achieved using currently available signal processing techniques. The number of data points in data 146 may be increased by increasing the rate at which pulsed laser beam 121 scans composite structure 104.

The rate at which pulsed laser beam 121 scans composite structure 104 may be increased by decreasing the spot size and increasing the pulse repetition rate of pulsed laser beam 121. Consequently, data 146 generated when pulsed laser beam 121 has a small spot size and a high repetition rate may have a higher signal-to-noise ratio as compared to when pulsed laser beam 121 has a larger spot size and a lower repetition rate.

The illustration of testing environment 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, in some cases, laser system 110 may be associated with movement system 111. In some illustrative examples, transmission system 118 may be considered part of movement system 111. In other illustrative examples, pulsed detection laser beam 142 may be configured to be emitted from a transmission system other than transmission system 118.

Figure 2:
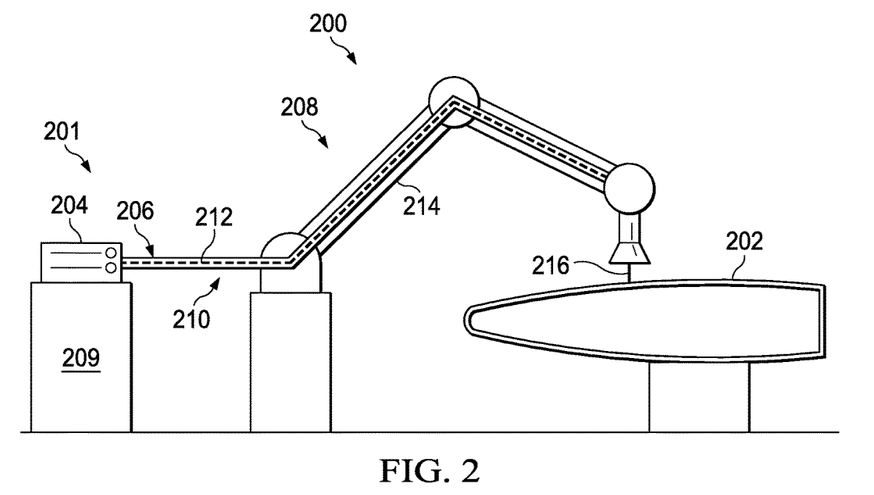
FIG. 2 is an illustration of a testing environment in accordance with an illustrative embodiment.

With reference now to FIG. 2, an illustration of a testing environment is depicted in accordance with an illustrative embodiment. In FIG. 2, testing environment 200 is an example of one implementation for testing environment 100 in FIG. 1. As depicted, laser ultrasound testing system 201 is configured to test composite structure 202.

Laser ultrasound testing system 201 is an example of one implementation for laser ultrasound testing system 102 in FIG. 1. Further, composite structure 202 is an example of one implementation for composite structure 104 in FIG. 1.

In this illustrative example, laser ultrasound testing system 201 includes generation laser system 204, transmission system 206, and movement system 208. Generation laser system 204 is an example of one implementation for generation laser system 114 in FIG. 1. Further, transmission system 206 and movement system 208 are examples of implementations for transmission system 118 and movement system 111, respectively.

As depicted, generation laser system 204 is mounted onto platform 209. Generation laser system 204 is configured to generate a pulsed laser beam that is carried through transmission system 206. Transmission system 206 takes the form of fiberoptic transmission system 210 in this example.

In particular, fiberoptic transmission system 210 includes number of optical fibers 212 configured to carry a pulsed laser beam.

Movement system 208 takes the form of robotic arm 214 in this illustrative example. Robotic arm 214 is configured to move such that the pulsed laser beam emitted from transmission system 206 may be directed in different directions.

For example, generation laser system 204 may generate a pulsed laser beam that is transmitted through transmission system 206 and emitted from transmission system 206 as pulsed laser beam 216. Pulsed laser beam 216 is an example of one implementation for pulsed laser beam 121 in FIG. 1. Robotic arm 214 is configured to control the direction in which pulsed laser beam 216 is pointed. In this manner, robotic arm 214 is configured to move such that pulsed laser beam 216 may be used to scan composite structure 202.

In this illustrative example, using fiberoptic transmission system 210 to transmit and emit pulsed laser beam 216 allows laser ultrasound testing system 201 to be used in various types of environments. For example, testing environment 200 may be a room, an area around an assembly line, an area in a factory, an outdoor area, an area on top of a countertop surface, or some other type of environment. Pulsed laser beam 216 is generated and emitted in a manner that does not require testing environment 200 to have extensive shielding.

Figure 3:
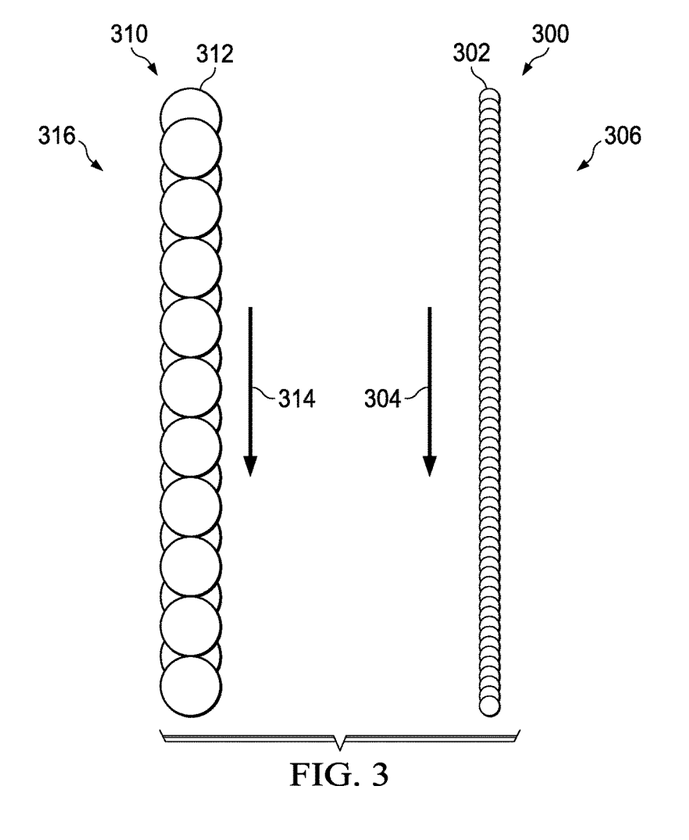
FIG. 3 is an illustration of two pulsed laser beams in accordance with an illustrative embodiment.

Turning now to FIG. 3, an illustration of two pulsed laser beams is depicted in accordance with an illustrative embodiment. In this illustrative example, pulsed laser beam 300 is an example of one implementation for pulsed laser beam 121 in FIG. 1.

Pulsed laser beam 300 forms spot 302. Spot 302 has a spot size less than about 1 millimeter (mm) in this example. Pulsed laser beam 300 may be moved in the direction of arrow 304 to form beam path 306.

Pulsed laser beam 310 is an example of a pulsed laser beam that may be formed using a currently available generation laser system such as, for example, a laser system that uses a gas laser source. Pulsed laser beam 310 forms spot 312. Spot 312 has a spot size that is about 5 millimeters (mm) in this example. Pulsed laser beam 310 may be moved in the direction of arrow 314 to form beam path 316.

As depicted, beam path 306 is narrower than beam path 316. The data that may be generated using beam path 306 allows a finer level of detail to be characterized than the data that may be generated using beam path 316. In this illustrative example, beam path 306 provides a finer level of detail in the ultrasound data because of a smaller excitation volume and allows the possibility of being able to utilize signal processing to improve spatial resolution to its limiting value.

Figure 4:
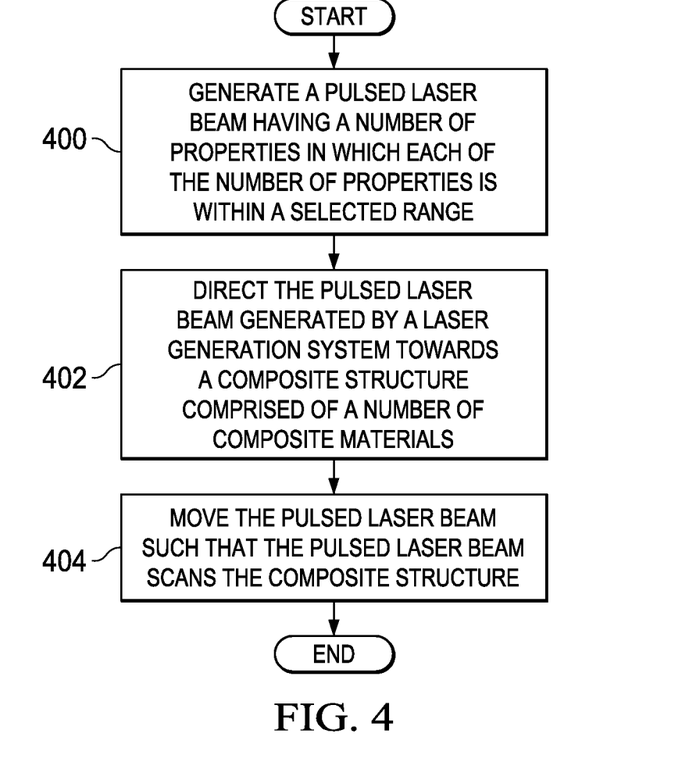
FIG. 4 is an illustration of a process for testing a composite structure in the form of a flowchart in accordance with an illustrative embodiment.

Turning now to FIG. 4, an illustration of a process for testing a composite structure in the form of a flowchart is depicted in accordance with an illustrative embodiment. The process illustrated in FIG. 4 may be implemented using laser ultrasound testing system 102 in FIG. 1.

The process begins by generating a pulsed laser beam having a number of properties in which each of the number of properties is within a selected range (operation 400). These properties may include at least one of, for example, without limitation, a pulse repetition rate, a spot size, an energy per pulse, and an absorption material.

Thereafter, the process directs the pulsed laser beam generated by a generation laser system towards a composite structure comprised of a number of composite materials (operation 402). In operation 402, a number of ultrasonic waves are formed in the composite structure when the pulsed laser beam contacts the composite structure without causing any undesired inconsistencies in the composite structure outside of selected tolerances.

Then, the process moves the pulsed laser beam such that the pulsed laser beam scans the composite structure (operation 404), with the process terminating thereafter. The ultrasonic waves formed in the composite structure as the pulsed laser beam scans the composite structure may be used to characterize the composite structure.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A system in a testing environment selected from the group consisting of a factory and an assembly line, the system comprising:
   a generation laser system configured to generate from a laser a pulsed laser beam having a number of properties wherein the number of properties includes at least a spot size of the laser less than about 1 millimeter, an optical fluence per pulse of between about 0.1 millijoules per centimeters squared to about 1000 millijoules per centimeters squared, and a pulse repetition rate between about 10,000 hertz and about 500,000 hertz;
   a transmission system configured to direct the pulsed laser beam generated by the generation laser system towards a composite structure comprised of a number of composite materials, wherein a number of ultrasonic waves are formed in the composite structure when the pulsed laser beam contacts the composite structure without causing any undesired inconsistencies in the composite structure outside of selected tolerances; and
   a movement system configured to control movement of the transmission system and the pulsed laser beam within the testing environment and to move the laser over the composite structure.

2. The system of claim 1, wherein a selected range for an energy per pulse is between about 1 microjoule and about 10,000 microjoules.

3. The system of claim 1, wherein the composite material includes a reinforcement material.

4. The system of claim 1, wherein the transmission system is a fiberoptic transmission system.

5. The system of claim 4, wherein the fiberoptic transmission system comprises:
a number of optical fibers configured to carry the pulsed laser beam.

6. The system of claim 1, wherein the movement system is a robotic arm.

7. The system of claim 1 further comprising:
a detection laser system configured to generate a pulsed detection laser beam towards the composite structure, wherein contact between the pulsed detection laser beam and the number of ultrasonic waves causes an alteration in a path of the pulsed detection laser beam; and
a detection system configured to detect the alteration, wherein the detection system comprises a number of detectors.

8. The system of claim 7, wherein the generation laser system, the detection laser system, and the transmission system are part of a laser system in the system.

9. A method for testing a composite structure in a testing environment selected from the group consisting of a factory and an assembly line, the method comprising:
generating a pulsed laser beam having a number of properties in which each of the number of properties is within a selected range, wherein the number of properties includes a spot size less than about 1 millimeter, an optical fluence per pulse between about 0.1 millijoules per centimeters squared to about 1000 millijoules per centimeters squared, and a pulse repetition rate between about 10,000 hertz and about 500,000 hertz;
moving, using a movement system, the laser over the composite structure within the testing environment;
directing the pulsed laser beam generated by the laser generation system towards the composite structure, wherein a number of ultrasonic waves are formed in the composite structure when the pulsed laser beam contacts the composite structure without causing any undesired inconsistencies in the composite structure outside of selected tolerances; and
determining whether an inconsistency is present in the composite structure using the number of ultrasonic waves.

10. The method of claim 9, wherein the number of properties additionally comprises:
an energy per pulse between about 1 microjoule and about 10,000 microjoules.

11. The method of claim 9, wherein the step of directing the pulsed laser beam comprises:
directing the pulsed laser beam towards the composite structure through a number of optical fibers in a fiberoptic transmission system.

12. The method of claim 9 further comprising:
determining whether the inconsistency is an undesirable inconsistency for the composite structure; and
responsive to detecting the undesirable inconsistency, reworking or discarding the composite structure in the testing environment.

13. The method of claim 12 wherein the movement system is a robotic arm.

14. The method of claim 9, further comprising:
generating a pulsed detection laser beam towards the composite structure;
altering a path of the pulsed detection laser beam when contact between the pulsed detection laser beam and a number of ultrasonic waves is detected; and
detecting the alteration.

15. The method of claim 14, wherein the alteration is detected using detectors.

* * * * *

UNITED STATES PATENT AND TRADEMARK OFFICE
CERTIFICATE OF CORRECTION

PATENT NO. : 9,625,423 B2  
APPLICATION NO. : 13/663855  
DATED : April 18, 2017  
INVENTOR(S) : Bossi et al.

Page 1 of 1

It is certified that error appears in the above-identified patent and that said Letters Patent is hereby corrected as shown below:

In the Claims

Column 9, Line 23, change "system in the system." to -- system in the laser ultrasound testing system. --

Signed and Sealed this  
Thirteenth Day of February, 2018

Andrei Iancu  
*Director of the United States Patent and Trademark Office*